United States Patent
Bazarov et al.

(10) Patent No.: US 6,772,637 B2
(45) Date of Patent: Aug. 10, 2004

(54) METHOD FOR IN-TUBE FLAW DETECTION

(75) Inventors: Alexandr J. Bazarov, Kolomna (RU); Alexandr P. Desyatchikov, Kolomna (RU); Nikolai A. Karasev, Kolomna (RU); Sergei P. Kirichenko, Kolomna (RU); Andrei M. Slepov, Kolomna (RU); Anatoly V. Smirnov, Kolomna (RU)

(73) Assignee: NGKS International Corp., Richmond Hill (CA)

( * ) Notice: Subject to any disclaimer, the term of this patent is extended or adjusted under 35 U.S.C. 154(b) by 0 days.

(21) Appl. No.: 10/232,182

(22) Filed: Aug. 30, 2002

(65) Prior Publication Data

US 2003/0061880 A1 Apr. 3, 2003

(30) Foreign Application Priority Data

Sep. 18, 2001 (RU) ........................................ 2001125488

(51) Int. Cl.[7] .......................... G01N 29/06; G01N 29/10
(52) U.S. Cl. ....................................................... 73/623
(58) Field of Search ........................... 73/623, 622, 602, 73/1.82, 866.5; 377/24.1

(56) References Cited

U.S. PATENT DOCUMENTS

| | | | |
|---|---|---|---|
| 3,810,384 A | * | 5/1974 | Evans ........................... 73/611 |
| 4,162,635 A | | 7/1979 | Triplett et al. |
| 4,909,091 A | | 3/1990 | Ellmann et al. |
| 5,062,300 A | | 11/1991 | Vallee |
| 5,497,661 A | | 3/1996 | Stripf et al. |
| 5,635,645 A | | 6/1997 | Ottes et al. |
| 6,474,165 B1 | * | 11/2002 | Harper et al. .................. 73/623 |

FOREIGN PATENT DOCUMENTS

| | | |
|---|---|---|
| EP | 0 271 670 B2 | 6/1988 |
| EP | 0 304 053 B1 | 2/1989 |
| EP | 0 561 867 B1 | 9/1993 |
| EP | 0 616 692 B1 | 9/1994 |
| EP | 0 684 446 A2 | 11/1995 |
| RU | 2018817 C1 | 8/1994 |
| RU | 2042946 C1 | 8/1995 |
| RU | 2108569 C1 | 4/1998 |
| WO | WO 96/13720 A1 | 5/1996 |

* cited by examiner

*Primary Examiner*—Hezron Williams
*Assistant Examiner*—Rose M. Miller
(74) *Attorney, Agent, or Firm*—Quarles & Brady LLP

(57) ABSTRACT

The claimed method of in-tube inspection of a pipeline is effected by passing through the pipeline an inspection pig carrying monitoring transducers responsive to the diagnostic parameters of the pipeline, means for measuring, processing and storage of the measurements data by periodic interrogation of the monitoring transducers during the travel of the inspection pig and processing and storage of the measurement data. The method is characterized in that during the travel of the pig with a period not less than the cycle time of the monitoring transducers the velocity of the inspection pig is determined, and the cycle time of the monitoring transducers is set as a function of at least two values of the pig velocity determined during its travel. The period of determining the inspection pig velocity makes 200–2000 cycles of interrogation of the monitoring transducers. The cycle of interrogation of the monitoring transducers is given a value from a number of discrete values in a series of at least 3. The realization of the claimed method allows one to avoid overflow of data storage module during a slow movement of the pig, as well as an unjustified change of the cycle time of the monitoring transducers at short-term changes of in the pig velocity.

11 Claims, 3 Drawing Sheets

METHOD FOR IN-TUBE FLAW DETECTION

CROSS REFERENCE TO RELATED APPLICATION

Not applicable.

STATEMENT REGARDING FEDERALLY SPONSORED RESEARCH OR DEVELOPMENT

Not applicable.

BACKGROUND OF THE INVENTION

Known in the present state of the art is a method for in-tube flaw detection (RU2018817—Aug. 30, 1994; RU2042946—Aug. 27, 1995; RU2108569—Apr. 10, 1998; U.S. Pat. No. 4,162,635—Jul. 31, 1979) by passing inside the pipeline the so-called "pig" or an inspection probe which carries reference transducers responsive to diagnostic parameters of pipelines, means for data measuring and processing, and for storing the measured data, by making periodical reference to said reference transducers which emit probing ultrasonic pulses and receiving respective reflected ultrasonic pulses.

Known in the art is another method for in-tube flaw detection (WO 96/13720—May 9, 1996 (relevant patent documents: U.S. Pat. No. 5,587,534, CA2179902, EP0741866, AU4234596, JP3058352);

EP0304053—Mar. 15, 1995 (relevant patent documents: U.S. Pat. No. 4,964,059, CA1292306, NO304398, JP1050903);

EP0271670—Dec. 13, 1994 (relevant patent documents: U.S. Pat. No. 4,909,091, CA1303722, DE3638936, NO302322, JP63221240);

EP0616692—Sep. 28, 1994 (relevant patent documents: WO93/12420, U.S. Pat. No. 5,635,645, CA2125565, DE4141123, JP2695702);

EP0561867—Oct. 26, 1994 (relevant patent documents: WO92/10746, U.S. Pat. No. 5,497,661, CA2098480, DE4040190)) based on a thickness metering technique. The method consists in passing the inspection pig provided with ultrasonic transducers, and means for measuring, processing, and storing the measured data, by periodically referring to said ultrasonic transducers that emit ultrasonic probing pulses, and by receiving respective reflected ultrasonic pulses, and by measuring the transit time of said pulses.

It is the repetition period of the ultrasonic probing pulse and the travel speed of the inspection pig (flaw detector) inside the pipeline that are responsible for longitudinal resolving power of the flaw detector. With a predetermined scanning period (i.e., the repetition period of probing pulses) the scanning increment depends on the travel speed of the inspection pig, i.e., the higher the pig travel speed the larger the scanning increment, and vice versa. The inspection pig travel speed in an oil pipeline or oil-product pipeline may amount to 2 m/s (an unsteady-state value up to 6 m/s), that in a gas pipeline, up to 10 m/s (provided that acoustic communication is established between the ultrasonic transducers and the pipeline wall using, e.g., a liquid plug). When the inspection pig is being passed through the pipeline, its travel speed changes, and in order that longitudinal resolving power be not in excess of a maximum permissible one, the repetition period of probing pulses is selected proceeding from a maximum travel speed of the inspection pig which is practicable when inspecting a particular pipeline.

As a result of changes in the inspection pig travel speed during its passing through the pipeline, an excessive scanning occurs on the travel portions where the inspection pig travel speed is decreased (with the preset rate of referring to the reference transducers), said excessive scanning resulting in an increased amount of measured data per unit length of pipeline and, accordingly, in unreasonable use of the data storage element.

Furthermore, dynamic scanning is performed, according to the method discussed above, whereby the scanning conditions depend on the inspection pig travel speed, as well as on the nature of changes in the travel speed of the flaw detector.

Known in the present state of the art is one more method for in-tube ultrasonic flaw detection of thin-walled pipes of heat-exchangers (U.S. Pat. No. 5,062,300—Nov. 5, 1991 (relevant patent documents: CA1301299, EP0318387, DE3864497, FR2623626, JP2002923)) by passing inside a pipeline a tube-mounted inspection pig having ultrasonic transducers and measurement means, said method consisting in periodically referring to ultrasonic transducers emitting ultrasonic probing pulses and receiving the respective reflected ultrasonic pulses, and processing the measured data. This method is characterized in that the period of referring to ultrasonic transducers, i.e., starting said transducers) is assumed as a function of the inspection pig travel speed inside the pipeline and set by rotating the probe head.

However, said method suffers from the disadvantage that instantaneous slip of the probe head (or odometer wheel) which is typical in inspection of oil-pipelines, results in skipping some pipeline portions due to zero probing signals when the probe head (or odometer wheel) is at standstill. Additionally, the method discussed above cannot be used for inspecting long-distance pipelines due to the fact that the probing device used for carrying out the method, lacks self-containing feature.

The prototype to the proposed method is a method for in-tube flaw detection (EP0684446—Nov. 29, 1995 (relevant patent documents: U.S. Pat. No. 5,460,046, JP7318336) by passing inside the pipeline the inspection pig which carries reference transducers responsive to the pipeline diagnostic parameters, means for measuring, processing, and storing the measured data, by making periodical reference to said reference transducers, processing and storing the data measured by said transducers.

The cardinal disadvantage inherent in said method resides in that an excessive scanning occurs on the travel portions where the inspection pig travel speed is decreased (with the preset rate of referring to the transducers), said excessive scanning resulting in an increased amount of measured data per unit length of pipeline and, accordingly, in unreasonable use of the data storage element.

The herein-proposed method for in-tube flaw detection is carried into effect by passing inside the pipeline the inspection pig which carries reference transducers responsive to the pipeline diagnostic parameters, means for measuring, processing, and storing the measured data, by making periodical reference to said reference transducers, processing and storing the data measured by said transducers.

The herein-proposed method differs from the prototype in that in the course of passing the inspection pig with a period not less than the period of referring to reference transducers, inspection pig travel speed is determined, and the period of referring to reference transducers is assumed as a function of at least two values of inspection pig travel speed found in the course of passing said inspection pig.

The main technical result attainable by realizing the proposed invention consists in that the fact of referring to reference transducers at a period of time depending on the speed of the inspection pig travel through the pipeline enables one to estimate the data storage capacity depending on the pipeline distance to be inspected, thereby avoiding overflow of data storage devices in the case of a decelerated motion of the inspection pig or its transitory jamming in the pipeline. Moreover, a change in the duration of the period of referring to ultrasonic transducers depending on at least two values of inspection pig travel speed determined in the course of passing said inspection pig allow of obviating an unjustified change in the duration of said period in the case of a short-time change in the inspection pig travel speed.

It is in the course of passing of the inspection pig at the abovementioned period of time (that is, the period of determining the inspection pig travel speed) that an average travel speed of the inspection pig is determined for a certain lapse of time not in excess of the period of determining the aforesaid average travel speed of the inspection pig.

Calculation of an average travel speed of the inspection pig for short lapses of time (on the order of 1 to 10 s) allows of avoiding an adverse effect of transient changes in the line speed on estimation of a required period of referring to the reference transducers.

The duration of the period of referring to the reference transducers is considered to be a function of an average inspection pig travel speed as determined for the aforesaid lapse of time and of at least one value of the average inspection pig travel speed as determined for a certain previous lapse of time.

Period of determining the aforestated inspection pig travel speed is assumed as a function of the aforementioned period of referring to reference transducers. Period of determining the aforestated inspection pig travel speed equals N the aforementioned periods of referring to reference transducers, the numerical value of N ranging from 200 to 2000.

Insofar as the period of referring to reference transducers is considered to be a function of a number of measured values of the inspection pig travel speed so as to keep stable resolving power throughout the pipeline distance, so fixing the instance of determining the inspection pig travel speed to the period of referring to reference transducers makes possible taking measurements of said travel speed as a function of time, thus providing uniform measurement of the pig travel speed along the pipeline distance. With the value of N exceeding 2000, with large periods of referring to reference transducers (respectively, with a low pig travel speed), and with an abrupt increase in the pig travel speed information about these facts will be less operative, with the result that no diagnostic information will be available from a respective the pipeline portion. On the other hand, with lower values of N and high pig travel speed the measured speed values will be distorted due to transient accelerations and vibrations.

The aforestated period of referring to reference transducers is given a value selected from several discrete values (at least three in number). To each of said discrete values of a period of referring to reference transducers corresponds the range of the aforestated inspection pig travel speed either average or instantaneous).

As a further development of the present invention, to each of the aforementioned discrete values of a period of referring to reference transducers corresponds a first range of the inspection pig travel speed, said range being used for changing (decreasing) the period of referring to reference transducers (repetition period of the probing pulses) (in the case of an increase in the pig travel speed for a certain lapse of time), and a second range of the inspection pig travel speed, said range being used for changing (increasing) the period of referring to reference transducers (repetition period of the probing pulses) (in the case of a decrease in the pig travel speed for a certain lapse of time).

Provision of two speed ranges for each value of the period of referring to reference transducers allows of realizing the hysteresis in the period/speed relationship. Thus, in cases where a certain threshold speed value is surpassed and the period of referring to reference transducers is reduced correspondingly, a reverse extension of said period occurs not until travel speed is reduced to a value less that the aforestated threshold value. This makes it possible to stabilize operation of all electronic devices and apparatus involved in measurements and conversion of measured data with an adequately uniform pig travel at a speed approximating the threshold value or slightly deviating therefrom.

The preferred embodiment of the proposed method is the one wherein the lower limit of a first speed range is in excess of the lower limit of a second speed range, the upper limit of a first speed range exceeds the upper limit of a second speed range, the lower limit of a first speed range is less than the upper limit of a second speed range, a difference between the lower limits of the first and second speed ranges and/or between the upper limits of the first and second speed ranges is not more than 0.5 m/s.

When the inspection pig travel speed decreases for a certain lapse of time within which the speed value goes beyond the limits of a respective speed range, the period of referring to reference transducers (repetition period of the probing pulses) is changed at a time delay of from 10 to 100 s.

The fulfillment of said condition allows one to assure an adequate resolving power in cases where the travel speed drops down but transiently (i.e., for a lapse of time below 10 s), whereas an increase in the period of referring to reference transducers for a lapse of time that follows immediately after the instance of measuring (determining) the travel speed (with a travel speed increasing just in said lapse of time would result in an undesirable increase in resolving power affecting adversely the latter.

As a further development of the present invention, in the course of passing the inspection pig ultrasonic probing pulses are emitted and reflected pulses are received, corresponding to said emitted pulses, the pulse repetition period of said probing pulses being in fact the aforementioned period of referring to reference transducers.

The aforementioned average travel speed for a certain lapse of time is determined by measuring the distance passed by the inspection pig inside the pipeline for said lapse of time, using one or more odometers.

In a preferred embodiment of the present invention said distance is measured using at least two odometers, by determining changes in reading of either of the odometers taken for the aforementioned lapse of time, whereupon the higher reading of the two one is adopted as the distance passed for said lapse of time. Next said higher odometer reading is recorded as an increment in the distance passed inside the pipeline, and said increment in the distance passed is used in the course of the aforementioned determining of an average travel speed for a certain lapse of time.

Use of the abovementioned algorithm for determining the inspection pig travel speed makes it possible to obviate negative effects resulting from slippage of either of the

BRIEF DESCRIPTION OF THE ACCOMPANYING DRAWINGS

DETAILED DESCRIPTION OF THE INVENTION

The herein-proposed method for in-tube ultrasonic flaw detection has been developed in the course of studies aimed at search for such technical solutions that allow the scope of the measured data per pipeline unit length when using in-tube inspection ultrasonic pigs (flaw detectors) for inspecting pipelines with a nominal diameter of from 10" to 56".

The ultrasonic thickness metering procedure consists in that ultrasonic pulses are emitted normally to the inside pipeline surface to be partially reflected from said surface, as well as from the outside pipeline surface, or from the flaw area, such as metal lamination in the pipe wall. Said ultrasonic pulses pass partially through the media interface made up by the outside pipeline wall. Having emitted the ultrasonic pulses, the ultrasonic transducers switch to the mode of reception of the reflected pulses and receive the pulses reflected from the inside wall, the pulses reflected from the outside wall, or the pulses reflected from said flaw area.

With a view to detecting cracks in the pipeline wall are emitted at an angle of about 17°–19° to the inside pipeline surface. Said pulses are partially reflected from the inside pipeline wall, from the outside wall thereof or from a crack-like flaw. Said ultrasonic pulses pass partially through the media interface or are reflected, thus attenuating the legitimate reflected signal.

Having emitted the ultrasonic pulses, the ultrasonic transducers switch to the mode of receiving the reflected pulses so as to receive the pulses reflected from the crack-like flaw.

The thus-obtained digital data on the time intervals corresponding to the transit time of the ultrasonic pulses and to pulse amplitudes are converted and recorded in the digital data storage device of an onboard computer.

A magnetic flaw detection of a pipeline wall consists in that a certain area of the pipeline wall is magnetized to the state of saturation, whereupon the magnetic field components nearby the magnetized pipeline wall area are measured using magnetic field transducers by making periodic reference to the latter (that is, by scanning said transducers). Presence of cracks or flaws concerned with loss of metal (due to corrosion or scores) results in a change in the magnitude and mode of distribution of magnetic induction.

An in-tube flaw detection is carried in a similar way by making periodical reference to other type transducers or sensors (such as magneto-optical transducers, optical sensors, electromagnetic-acoustical transducers, pipeline cross-sectional profile transducers by, e.g., periodically referring to transducers sensing angle-of-turn of levers pressing against the pipeline inside surface, and also to some other transducer types).

Figure 1:
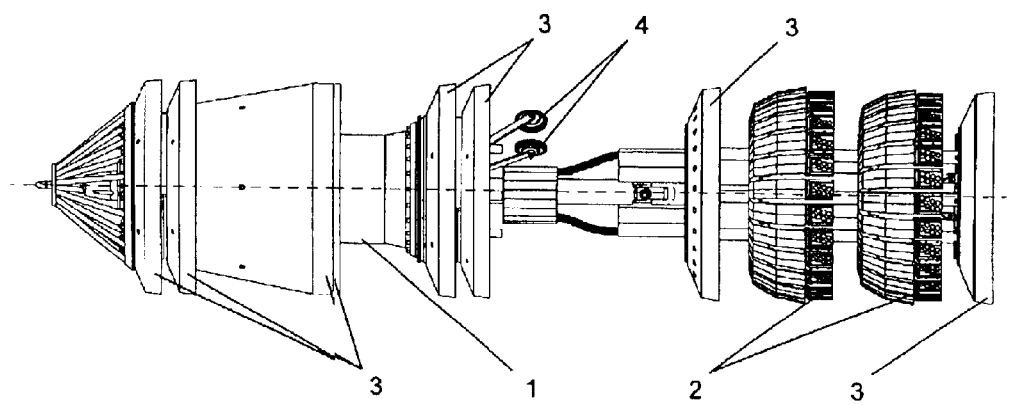
FIG. 1 illustrates one of the embodiments of construction arrangement of the present in-tube ultrasonic flaw detector.

Given below is an exemplary embodiment of the herein-proposed method for in-tube ultrasonic flaw detection using an in-tube ultrasonic flaw detector for inspecting a pipeline having a diameter of 38"–56" and a wall thickness of from 4.0 to 23.5 mm, one of the preferred construction arrangement thereof being illustrated in FIG. 1. In one of its preferred embodiments the flaw detector (ultrasonic inspection pig) withstands a fluid medium pressure up to 80 atm at a transmission capacity of about 85-percent nominal pipeline diameter, at a temperature of the fluid being handled from zero to +50° C. and a minimum negotiable turning radius of about 1.5 pipeline diameters. Provision is made in the inspection pig for the following types of explosion protection: "Explosion-tight enclosure" and "Special type of explosion protection". The ultrasonic inspection pig comprises a casing 1 which makes up an explosion-tight enclosure accommodating a power source and electronic equipment operating on the basis of an onboard computer which controls the operation of the ultrasonic inspection pig during its travel inside the pipeline. The electronic equipment comprises devices for measuring, processing, and storing the measured data. Used as said power source are storage batteries or batteries of galvanic cells having a total capacity up to 1000 Ah.

The tail portion of the ultrasonic inspection pig accommodates ultrasonic transducers 2 adapted to alternately emit and receive ultrasonic pulses. The polyurethane sealing rings 3 mounted on the pig body provide centering of the pig inside the pipeline and its movement with the flow of the fluid medium pumped through the pipeline. The wheels of the odometers 4 installed on the pig body are pressed against the internal wall of the pipeline. During the pig travel the information on the passed distance measured by the odometers is recorded in the storage device of the onboard computer and after performing the diagnostic scanning and processing of the accumulated data allows one to determine the position of the flaws on the pipeline and, respectively, the place of subsequent excavation and repair of the pipeline.

The device operates as follows.

Figure 2:
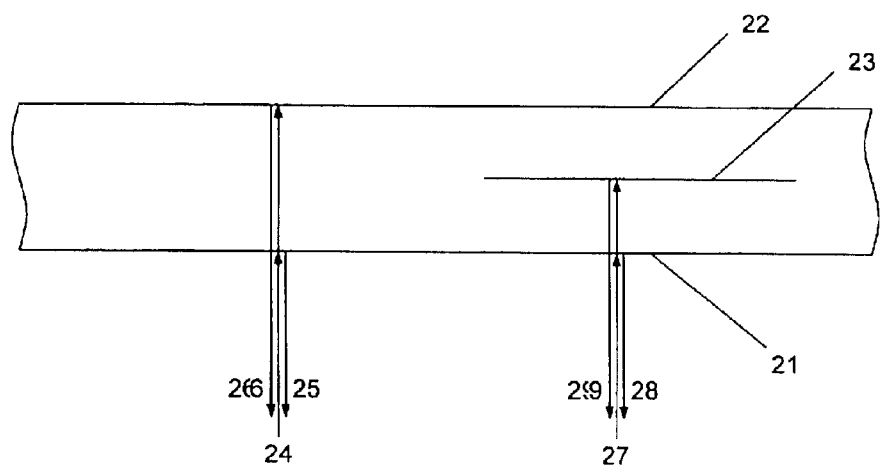
FIG. 2 is a diagram showing the transfer of the ultrasonic probing pulses on a faultless section of the pipe and on a faulty section with a flaw such as "lamination"

The inspection pig is placed into the pipeline and the pump for transferring the product being handled (oil or oil product) through the pipeline is switched on. In the course of travel of the inspection pig inside the pipeline the ultrasonic transducers periodically emit ultrasonic pulses 24, 27 (FIG. 2) which are partially reflected from the pipeline inside wall 21, from the outside wall 22 or from the flaw area 23, for example, metal lamination in the pipe wall. Having emitted the ultrasonic pulses, the ultrasonic transducers switch to the mode of reception of the reflected pulses and receive the pulses 25, 28 reflected from the inside wall, the pulses 26 reflected from the outside wall or the pulses 29 reflected from said flaw area.

The electric pulse triggering the ultrasonic transducer for emitting ultrasonic pulses, simultaneously triggers the counter to count the time interval between the instance of emitting the ultrasonic pulse and the instance of receiving the ultrasonic pulse reflected from the inside wall of the pipeline. The electric pulse detected by the signal processing devices as an ultrasonic pulse, received by the ultrasonic transducer, makes the counter stop counting the time interval corresponding to the travel of the ultrasonic pulse to the inside wall and back and simultaneously triggers the counter to count the time interval between the instance of receiving the ultrasonic pulse reflected from the inside wall of the pipeline and the instance of receiving the respective ultrasonic pulse reflected from the outside wall of the pipe or from the flaw area.

The thus-obtained digital data on the time intervals corresponding to the transit time of the ultrasonic pulses are converted and recorded in the digital data storage device of the onboard computer, said storage device being built around solid-state storage elements.

Figure 3:
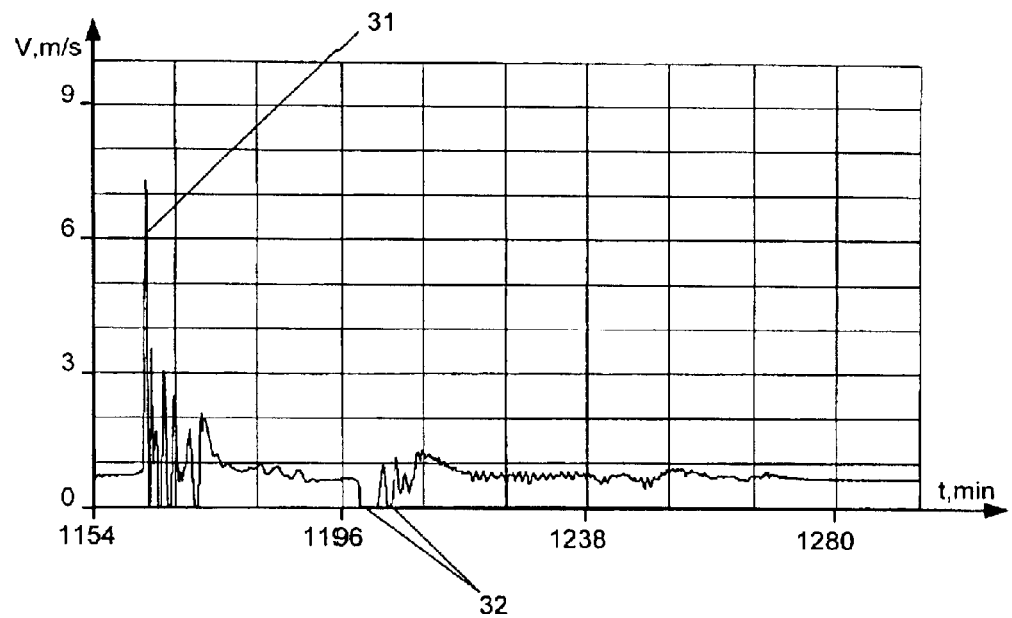
FIG. 3 is a graphic representation of the inspection pig travel speed inside the pipeline vs the travel time along a certain portion of the inspected pipeline.

FIG. 3 represents the inspection pig travel speed V inside the pipeline, expressed in meters per second, vs the time 't' of the pig travel, expressed in minutes. With the speed at which the pig traveled for a majority of the traveling time (about 0.8 ms), the repetition period of the probing pulses should not be in excess of 4.1 ms. With the pig travel speed of about 7.2 m/s (as shown in Ref. No. 31) and a maximum resolving power of 3.3 mm lengthwise the pipeline, the repetition period of the probing pulses should not be in excess of 0.46 ms. With an invariable repetition periods of the probing pulses equal to 4.1 ms, an overspeed as shown in Ref. No. 31 would result in data loss for a pipeline portion exceeding 50 m. On the other hand, performing in-tube inspection with a pulse repetition period of 0.46 ms would provide no data loss, but the amount of measured data would be 8 or 9 times as high with a 0.4 mm resolution on the main pipeline portion, and the same times lower that is sufficient for flaw detection and determining the flaw parameters in subsequent data processing (the more so as under strong inspection pig deceleration shown in Ref. No. 32).

Figure 4:
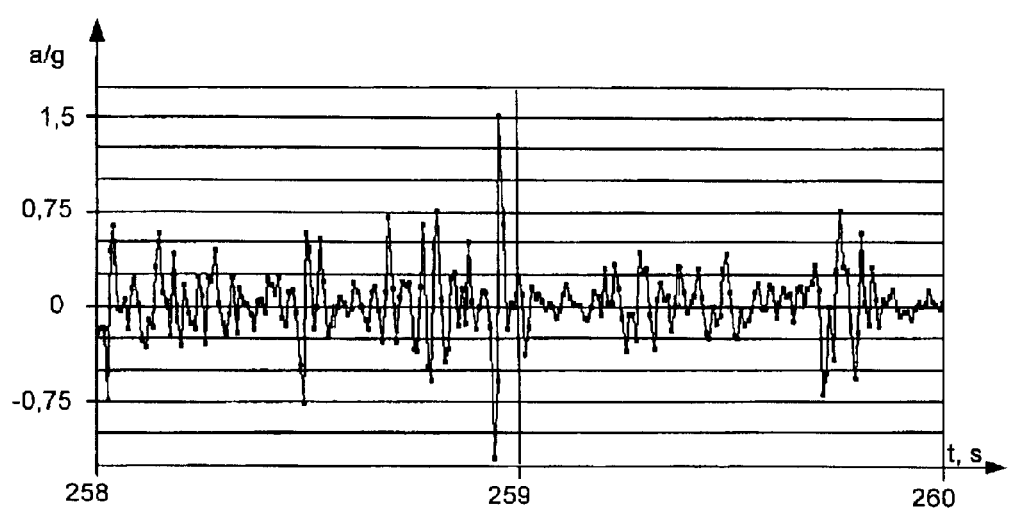
FIG. 4 is a graphic representation of the longitudinal linear acceleration of the inspection pig inside the pipeline vs its travel time for a certain portion of the inspected pipeline.

FIG. 4 represents the longitudinal linear pig acceleration 'a' inside the pipeline, expressed in free fall acceleration units 'g' vs the time 't' of the pig travel, expressed in seconds. According to one of the preferred embodiments of the invention, in the course of passing with a period equal to 512 repetition periods of the probing pulses there is determined an average pig travel speed for said 512 periods.

Said pig travel speed is determined by measuring the distance traveled by the pig inside the pipeline for said lapse of time, using two odometers. In this case, there is determined a change in the reading of each of said two odometers for said lapse of time, whereupon the greater of said two values is adopted as the distance passed by the pig for said lapse of time.

Thereupon said greater value is recorded in the storage device as an increment of the distance traveled by the pig inside the pipeline. The onboard computer disposed in the inspection pig calculates an average pig travel speed V for said lapse of time, $V_n$ being the nth measured pig travel speed.

For each n-th measurement (determination) of the pig travel speed, the functional pig speed $V_{f,s}$ is calculated, using the following recurrence relation:

$$V_{f,s} = K*V_n + V_{f,n-1}/(K+1)$$

where $V_{f,n-1}$ is the functional speed calculated at the preceding (n−1)th pig speed measurement;

the quantity K takes on either of the two values depending on the sign of the difference $\Delta V_n$ between the nth measured pig speed $V_n$ and the pig speed determined at the (n−1)th measurement of the functional speed $V_{f,n-1}$.

$$\Delta V_n = V_n - V_{f,n-1}$$

K=0.1 with $\Delta V_n<0$, K=0.5 with $\Delta V_n>0$.

Having calculated the value of the functional speed $V_{f,n}$, one should determine to what speed range relates the speed value found.

Hence according to the preferred embodiment of the invention carried into effect, the repetition period of the probing ultrasonic pulses may take on eight numerical values, namely, 1.66 ms, 2.05 ms, 2.5 ms, 3.3 ms, 4.67 ms, 8.22 ms, 16.45 ins, and 54.85 ms.

Two ranges of the pulse repetition period correspond to each of said eight numerical values.

| Repetition period of probing pulses, ms | Speed range for decreasing pulse repetition period (when pig speed increases) m/s | Speed range for increasing pulse repetition period (when pig speed decreases) m/s |
| --- | --- | --- |
| 1.66 | >1.76 | >1.6 |
| 2.05 | 1.43–1.76 | 1.3–1.6 |
| 2.5 | 1.1–1.43 | 1.0–1.3 |
| 3.3 | 0.79–1.1 | 0.7–1.0 |
| 4.67 | 0.46–0.79 | 0.4–0.7 |
| 8.22 | 0.25–0.46 | 0.2–0.4 |
| 16.45 | 0.1–0.25 | 0.06–0.2 |
| 54.85 | 0.0–0.1 | 0.00–0.06 |

To each of said discrete (numerical) value of the probing pulse repetition period corresponds the first pig speed range used when the pig travel speed is increased within a certain lapse of time, and the second pig speed range used when the pig travel speed is decreased within a certain lapse of time.

For all the eight values of the probing pulse repetition period the lower limit of the first speed range exceeds the lower limit of the second speed range and the upper limit of the first speed range exceeds the upper limit of the second speed range.

Apart from that, the lower limit of the first speed range is less than the upper limit of the second speed range.

A difference between the lower limits of the first and second speed ranges and/or between the upper limits of the first and second speed ranges is not more than 0.5 m/s.

Otherwise speaking, two threshold values correspond to each of the aforesaid eight probing pulse repetition periods.

| Repetition period of probing pulses, ms | Threshold speed value for decreasing pulse repetition period (when pig speed increases), m/s | Threshold speed value for increasing pulse repetition period (when pig speed decreases, m/s |
| --- | --- | --- |
| 1.66 | — | 1.6 |
| 2.05 | 1.76 | 1.3 |
| 2.5 | 1.43 | 1.0 |
| 3.3 | 1.1 | 0.7 |
| 4.67 | 0.79 | 0.4 |
| 8.22 | 0.46 | 0.2 |
| 16.45 | 0.25 | 0.06 |
| 54.85 | 0.1 | — |

The used ratio between the dependence of the pig travel speed $V_{f,n}$ on the measured speed values results in functional relationship characterized in that when the inspection pig travel speed decreases for a certain lapse of time within which the speed value goes beyond the limits of a respective speed range, the probing pulse repetition period is changed at a time delay of from 10 to 100 s depending on the pulse repetition period and hence the period of determining the pig travel speed.

Thus, with a decrease in the pig travel speed, the ratio between $dV_{f,n}$ and $dV_n$ is 0.091; whence a change in the pig travel speed per speed measurement procedure causes a change in the functional travel speed less by one order of magnitude so that a change in the functional speed equal to the steady-state change in the measured value of the pig travel speed and, accordingly, a change in the probing pulse repetition period occurs tentatively in ten periods of speed measurement. With a typical probing pulse repetition period of 3.3 ms (which corresponds to a pig travel speed of about 1 m/s) and a speed measurement period equal to 512 probing pulse repetition periods, said change occurs in approximately 20 s.

With an increase in the pig travel speed, the ratio between $dV_{f,n}$ and $dV_n$ is 0.33; whence a change in the probing pulse repetition period occurs approximately four times as fast as in the case of speed decrease.

On terminating the inspection of the preset pipeline portion the inspection pig is withdrawn from the pipeline, and the data obtained in the course of the diagnostic passing are transferred to a computer outside of the inspection pig.

Subsequent analysis into the measured and recorded data makes possible identifying pipeline wall flaws and defining their position on the pipeline with a view to performing repair of the faulty pipeline portions.

Figure 5:
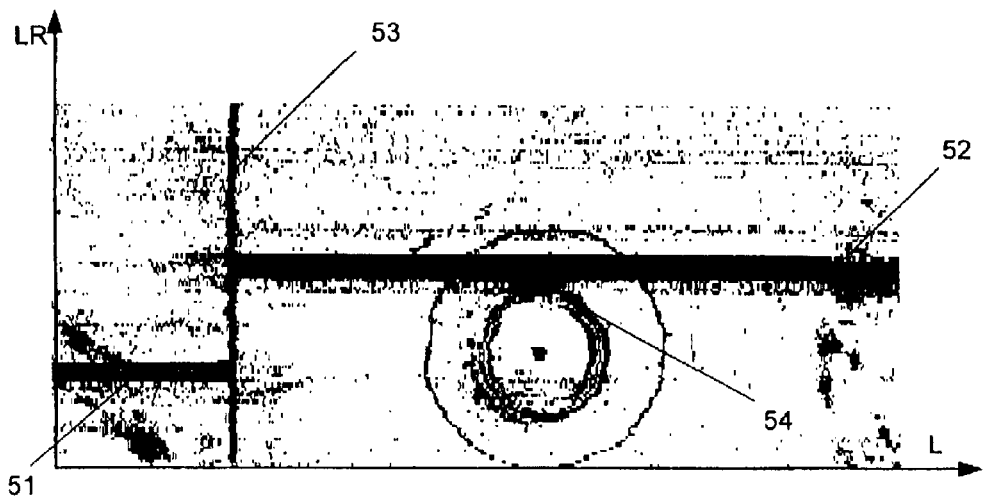
FIG. 5 is a graphic representation of the measured data on the pipeline wall thickness for a certain portion of the inspected pipeline, allowing the weld joints to be identified.
Figure 6:
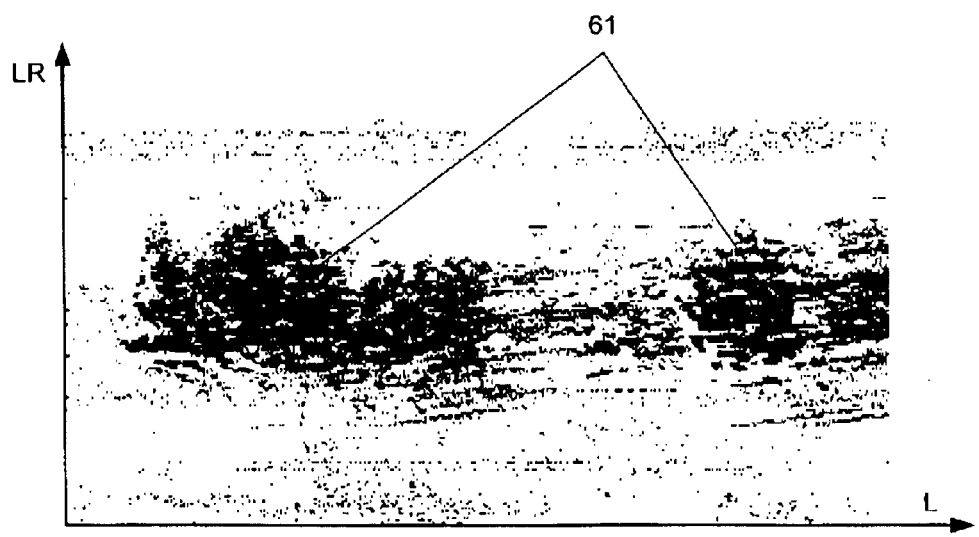
FIG. 6 is a graphic representation of the measured data on the pipeline wall thickness for a certain portion of the inspected pipeline, allowing corrosion loss of metal to be identified.

FIGS. 5 and 6 represent the fragments of the graphic representation of the data resultant from a diagnostic passing of the ultrasonic inspection pig and allowing specific features of a given pipeline and the flaws in its walls to be identified. The pipeline distance is plotted along the axis L in FIGS. 6 and 7 and the length along its perimeter is plotted on the axis LR. The black dots on the image show that at these spots on the pipe the difference between the measured value of the wall thickness and the nominal value for the given section of the pipeline exceeds a certain preset threshold value. FIG. 5 presents the typical features of the pipelines, that is, longitudinal weld joints 51 and 52 of the pipes, a weld joint between the pipes 53, and an air bleed cock 54. FIG. 6 illustrates typical corrosive flaws 61 on the pipe and detected as a result of performing the in-tube ultrasonic flaw detection using the herein-proposed method.

What is claimed is:

1. A method for in-tube flaw detection in a pipeline, comprising:
    passing inside the pipeline an inspection pig carrying transducers responsive to at least one pipeline diagnostic parameter, the transducers alternately emitting probing pulses and receiving reflected pulses corresponding to the probing pulses, the emitting of probing pulses occurring at a pulse repetition period;
    reading data from said transducers, and processing and storing the data measured by said transducers,
    determining periodically during the passing a travel speed of the inspection pig with a period of determining the travel speed that is greater than the pulse repetition period; and
    varying during the passing the pulse repetition period as a function of the determined value of the pig travel speed and as a function of at least one value of the pig travel speed determined for the passing for a selected preceding lapse of time.

2. The method of claim 1, further comprising determining an average travel speed of the inspection pig for a selected lapse of time in the course of passing the inspection pig, determining the pulse repetition period for the passing as a function of the average travel speed over the selected lapse of time and as a function of at least one average travel speed determined for a selected preceding lapse of time.

3. The method of claim 1, further comprising determining the period of determining the travel speed as a function of the pulse repetition period.

4. The method of claim 3, wherein the period of determining the travel speed is selected to equal N periods of the pulse repetition period, the numerical value of N ranging from 200 to 2000.

5. The method of claim 1, wherein the pulse repetition period is selected from a range of at least three discrete period values, each of the discrete period values corresponds to a first range of inspection pig travel speeds for decreasing the pulse repetition period in the case of an increase in the pig travel speed for a certain lapse of time, and to a second range of the inspection pig travel speeds for increasing the pulse repetition period in the ease of a decrease in the pig travel speed for a certain lapse of time.

6. The method of claim 1, wherein the pulse repetition period is selected from a range of at least three discrete period values,
    each of said discrete period values corresponds to a range of inspection pig travel speeds,
    under decreasing the inspection pig travel speed for a certain lapse of time within which the speed value goes beyond the limits of a respective speed range, the pulse repetition period of is changed at a time delay of from 10 to 100 s.

7. The method of claim 1, wherein the pulse repetition period is selected from a range of at least three discrete period values,
    each of said discrete period values corresponds to a range of inspection pig travel speeds,
    for each n-th determination of the pig travel speed, the functional pig speed $V_{f.s}$ is calculated, using the following recurrence relation $V_{f.s}=K*V_n+V_{f.n-1}(K+1)$, where $V_n$ being the nth measured pig travel speed, $V_{f,n-1}$ is the functional speed calculated at the preceding (n-1)th pig speed determination, the quantity K takes on positive value,
    having calculated the value of the functional speed $V_{f,n}$, one should determine to what speed range relates the speed value found.

8. The method of claim 7, wherein the quantity K takes on either of the two values K=0.1 or K=0.5.

9. The method of claim 7, wherein the quantity K takes on either of the two values depending on the sign of the difference $\Delta V_n$ between the nth measured pig speed $V_n$ and the functional pig speed determined at the (n-1)th determination of the functional speed $V_{f,n-1}$: $\Delta V_n - V_{f,n-1}$, K=0.1 with $\Delta V_n<0$, K=0.5 with $\Delta V_n>0$.

10. The method of claim 5, wherein a lower limit of the first speed range exceeds a lower limit of the second speed range, an upper limit of the first speed range exceeds an upper limit of the second speed range, the lower limit of the first speed range is less than the upper limit of the second speed range.

11. The method of claim 10, wherein the difference between the lower limit of the first speed range and the lower limit of the second speed range is less than 0.5 m/s, the difference between the upper limit of the first speed range and the upper limit of the second speed range is less than 0.5 m/s.

* * * * *

UNITED STATES PATENT AND TRADEMARK OFFICE
CERTIFICATE OF CORRECTION

PATENT NO. : 6,772,637 B2
DATED : August 10, 2004
INVENTOR(S) : Alexandr J. Bazarov et al.

It is certified that error appears in the above-identified patent and that said Letters Patent is hereby corrected as shown below:

<u>Column 8,</u>
Line 14, "ins" should read -- ms --.

<u>Column 10,</u>
Line 18, "ease" should read -- case --.
Line 18, "of is" should read -- is --.
Line 37, "(K+1)" should read -- /(K+1) --.

Signed and Sealed this

Nineteenth Day of April, 2005

JON W. DUDAS
*Director of the United States Patent and Trademark Office*